US00PP35395P2

(12) United States Plant Patent
Benedicto Artigot et al.

(10) Patent No.: US PP35,395 P2
(45) Date of Patent: Sep. 26, 2023

(54) LEMON PLANT NAMED 'BENEDICTO'

(50) Latin Name: ***Citrus limon* (L.) Burm. f.**
Varietal Denomination: BENEDICTO

(71) Applicants: Martin Benedicto Artigot, Pilar de la Horadada (ES); Victoria Eugenia Alessandrello Benedicto, Pilar de la Horadada (ES)

(72) Inventors: Martin Benedicto Artigot, Pilar de la Horadada (ES); Victoria Eugenia Alessandrello Benedicto, Pilar de la Horadada (ES)

(73) Assignee: ICOTEA INMOB, S.L, Pilar de la Horadada (ES)

( * ) Notice: Subject to any disclaimer, the term of this patent is extended or adjusted under 35 U.S.C. 154(b) by 4 days.

(21) Appl. No.: 17/945,564

(22) Filed: Sep. 15, 2022

(51) Int. Cl.
*A01H 5/08* (2018.01)
*A01H 6/78* (2018.01)

(52) U.S. Cl.
USPC ..... Plt./201
CPC ..... *A01H 6/785* (2018.05)

(58) Field of Classification Search
USPC ..... Plt./201
CPC ..... A01H 6/785; A01H 5/08
See application file for complete search history.

(56) References Cited

PUBLICATIONS

Sublim Variedad Gestionada Por:Variety Managed By CVVP with English Translation uploaded to CVVP webpage Sep. 17, 2021. (2 pages).

*Primary Examiner* — Keith O. Robinson
(74) *Attorney, Agent, or Firm* — WHDA, LLP

(57) ABSTRACT

'BENEDICTO' is an early, seedless, thin-skinned lemon. The tree is thornless on stems and shoots, with large leaves and short internodes, vigorous and high yield efficiency.

7 Drawing Sheets

Latin name of the genus and species of the plant claimed: *Citrus limon* (L.) Burm. f.

Variety denomination: Lemon plant 'BENEDICTO'.

BACKGROUND OF THE INVENTION

The new and distinct lemon cultivar of the present invention was discovered while growing in a country state of the Alicante region of Spain called "La Alcoraya" while present among standard 'Fino 95' lemon trees (non-patented). A single plant of the new cultivar was found in 2012, was carefully preserved and subsequently asexually reproduced by grafting on different standard rootstocks (non-patented) until it was found that the best rootstock was the *C. macrophylla*. Once known that, the variety was propagated in other country state of the Alicante region called "Lo Monte" in order to confirm that the variety is distinct, uniform and stable.

The new invention called 'BENEDICTO' is seedless in the main harvest, contains more juice than existing varieties, is significantly thinner peel, can harvest earlier than existing varieties, is thornless on stems and shoots, has large leaves and short internodes, is vigorous and high yielding efficiency, and produces regular bearing.

The 'Fino 95' and 'Fino 49' varieties are grown on "Lo Monte," so the comparative studies have been carried out under homogeneous growing and climatic conditions, and the characteristics described have been found to be attributable to the genotype.

Had the new cultivar of the present invention not been discovered and preserved it would have been lost to mankind. This new cultivar is believed to be a spontaneous mutation of the 'Fino 95' lemon tree of unknown causation.

It was found that the new lemon cultivar of the present invention forms attractive fruit which when compared to the 'Lemon 95' (non-patented) or "Lemon 48" (non-patented) cultivars displays an earlier season of maturity.

The new cultivar has been asexually reproduced in the Alicante region of Spain by grafting on *C. macrophylla* rootstock. The combination of the characteristics, including the early maturity fruit, has been shown to be stable and is reliably transmitted to succeeding generations following such asexual reproduction. Accordingly, the new cultivar reproduces in a true-to-type manner by such asexual reproduction.

The new cultivar can be readily distinguished from 'Lemon 95' because its seedless (while in the 'Fino 95' and 'Fino 49' varieties the presence of seeds affects between 12-82% of the fruit, reaching average values of 6.06 seeds per fruit in 'Fino 49') and thornless on stems and shoots, the leaves are larger, it produces up to 7.92% more juice and the peel is significantly thinner.

SUMMARY OF THE INVENTION

Noticeable characteristics of the inventive variety 'BENEDICTO' are as follows:

(1) 'BENEDICTO' is seedless in the main harvest and has a significantly thinner peel than existing varieties.

(2) 'BENEDICTO' has significantly more juice than existing varieties.

(3) 'BENEDICTO' has thornless stems and shoots, and therefore it can be easily harvested manually without the use of a harvesting device.
(4) 'BENEDICTO' has large leaves and short internodes than existing varieties, and therefore it is less susceptible to growth inhibition than the existing varieties.
(5) 'BENEDICTO' is vigorous and high yield efficiency.
(6) 'BENEDICTO' produces regular bearing year after year.

DETAILED DESCRIPTION OF THE INVENTION

Figure 1:
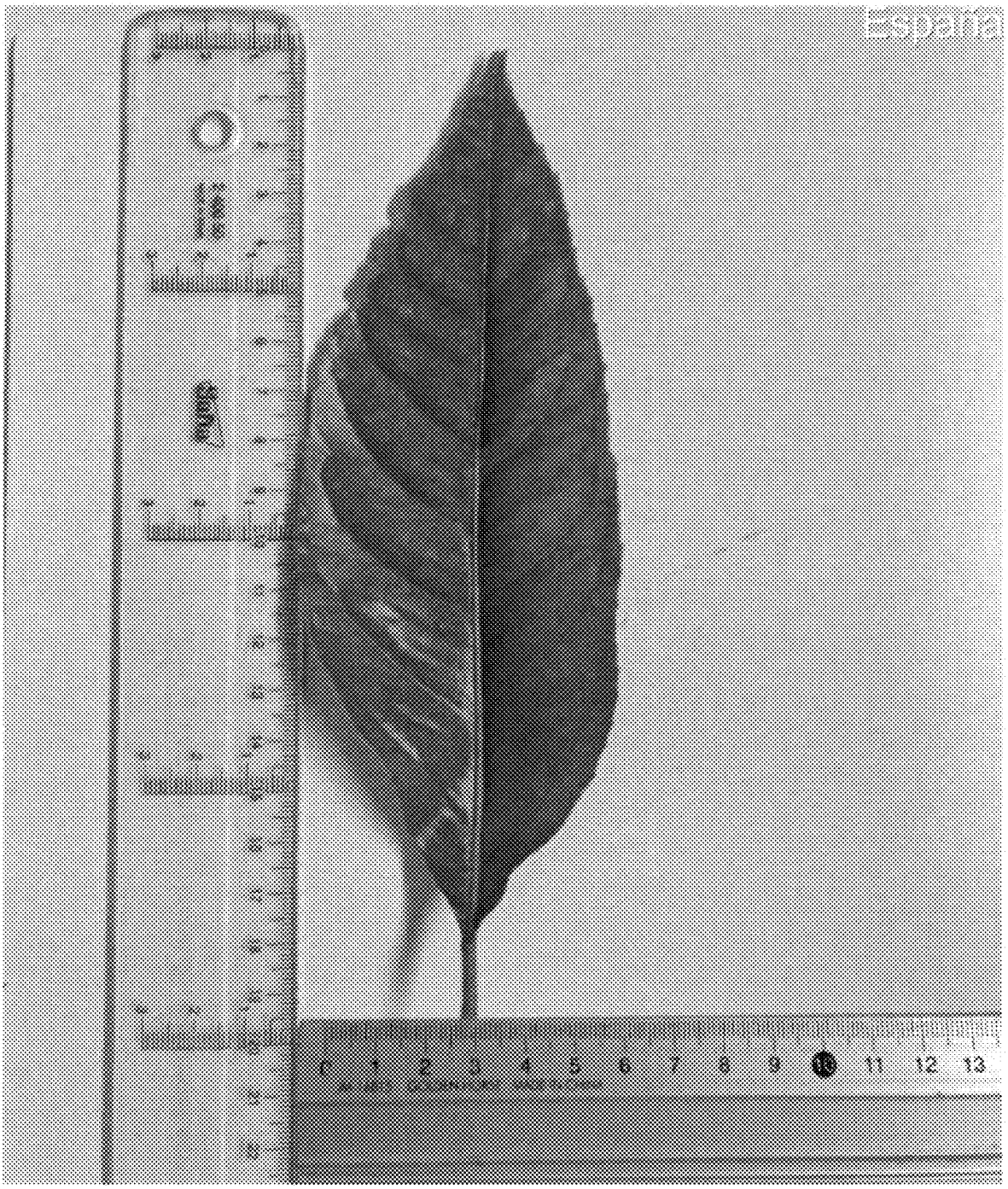
FIG. 1 is a photograph showing a front view of a leaf of 'BENEDICTO.'
Figure 2:
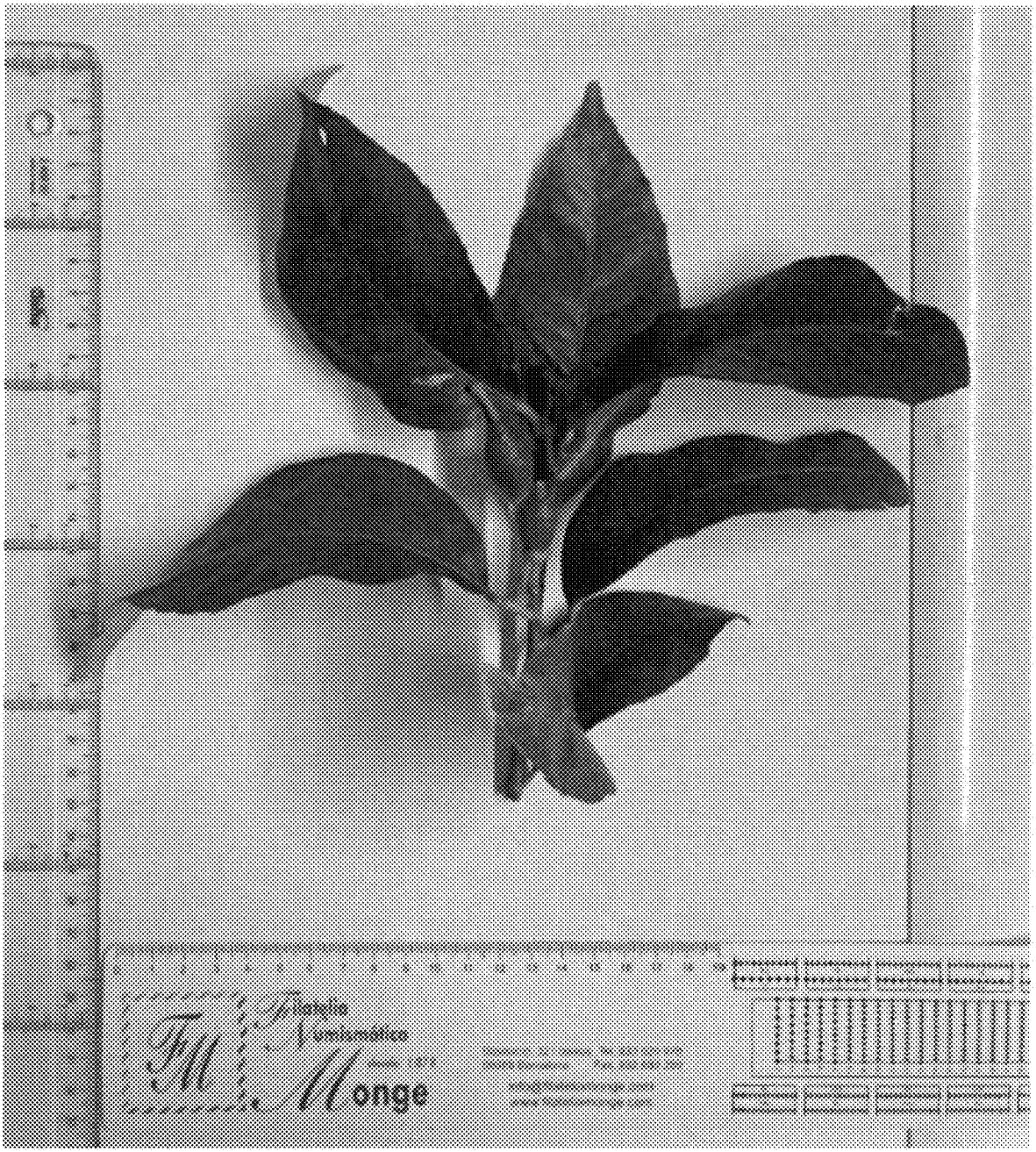
FIG. 2 is a photograph of a small piece of branch showing the leaves and the fruit emerging.
Figure 3:
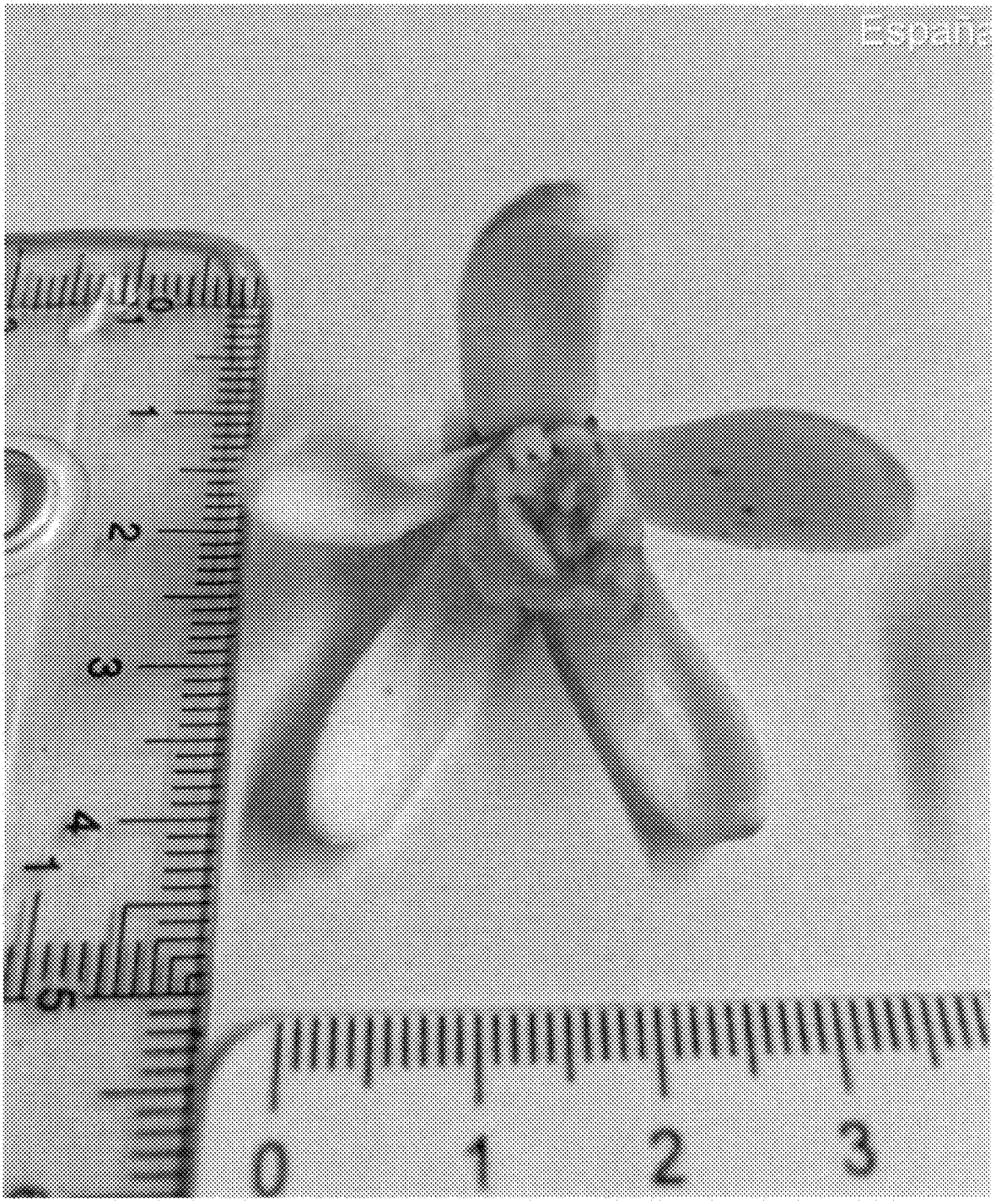
FIG. 3 is a photograph showing a top view of a flower of 'BENEDICTO.'
Figure 4:
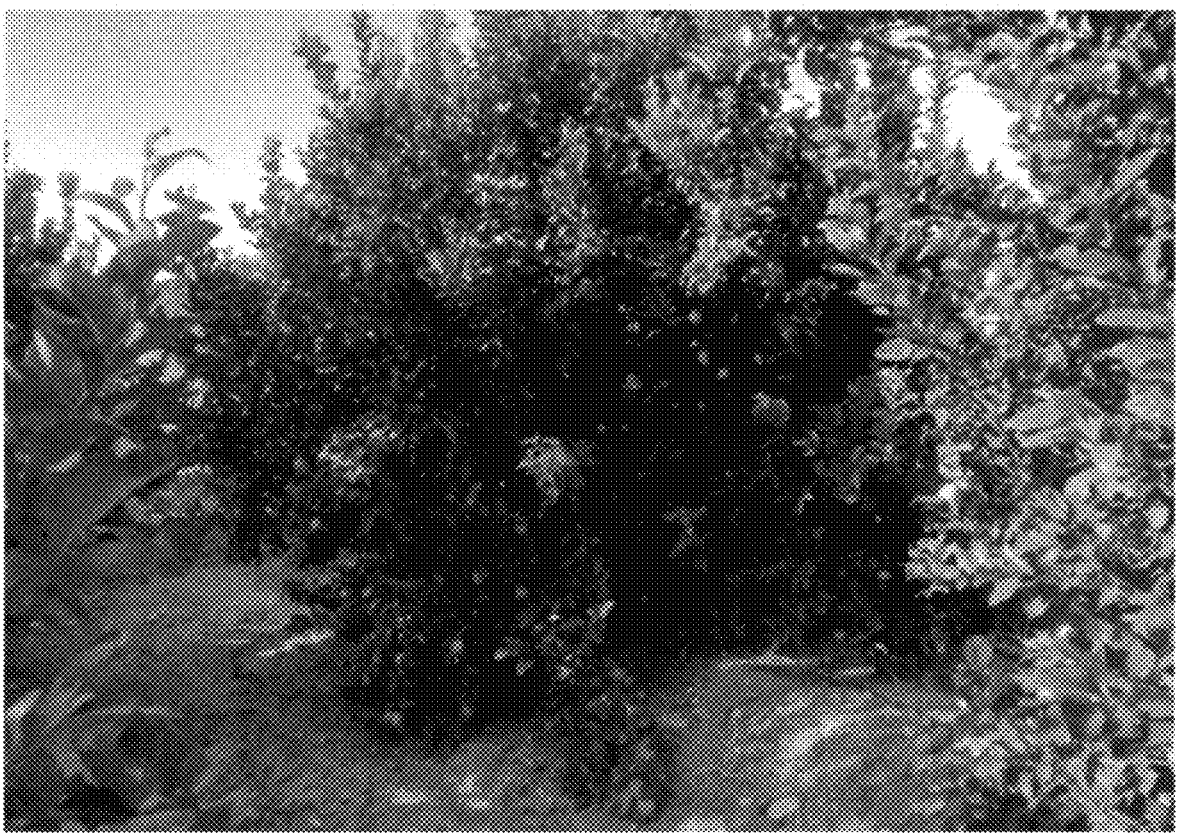
FIG. 4 is a photograph showing the overall relatively dense and spreading growth habit of a typical specimen of the new cultivar that was grafted with this new variety in April 2015 and observation obtained during the growing season of 2021.
Figure 5:
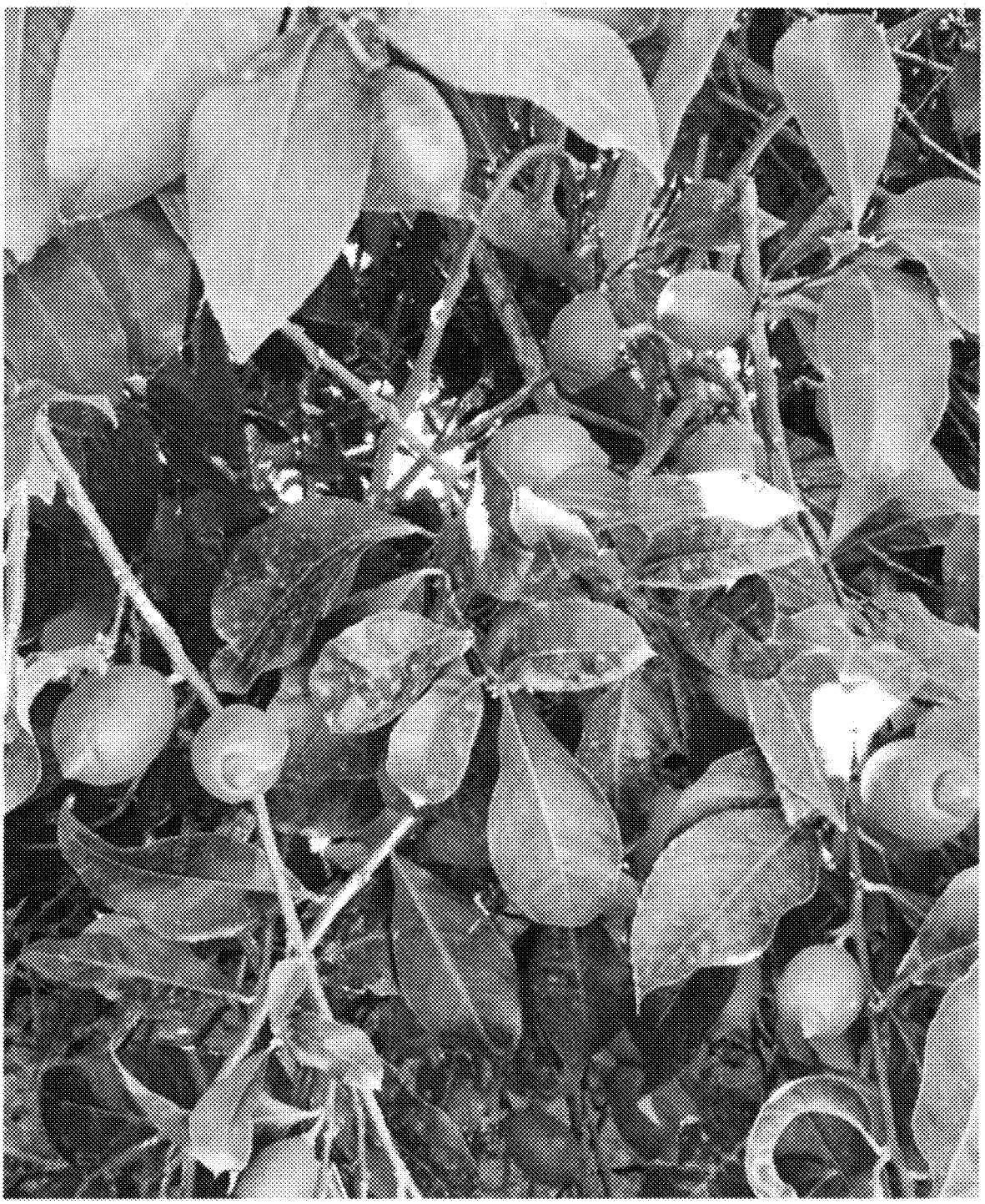
FIG. 5 is a photograph showing a closer view of the foliage and the abundant formation of immature fruit that is in process of ripening while present on a typical specimen of the new cultivar that was grafted with this new variety in April 2015 and observation obtained during the growing season of 2021. The same or a comparable tree to that of FIG. 4 is being depicted.
Figure 6:
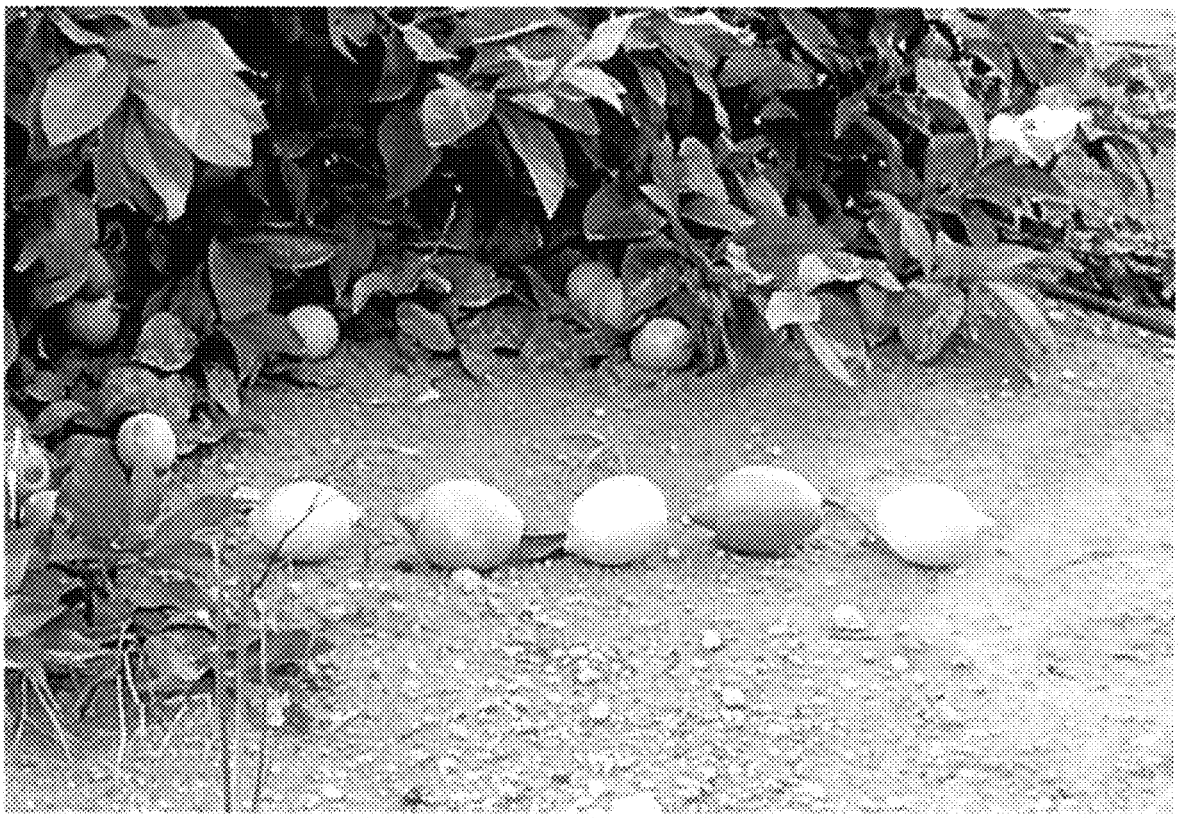
FIG. 6 is a photograph showing the fruit body of 'BENEDICTO.'
Figure 7:
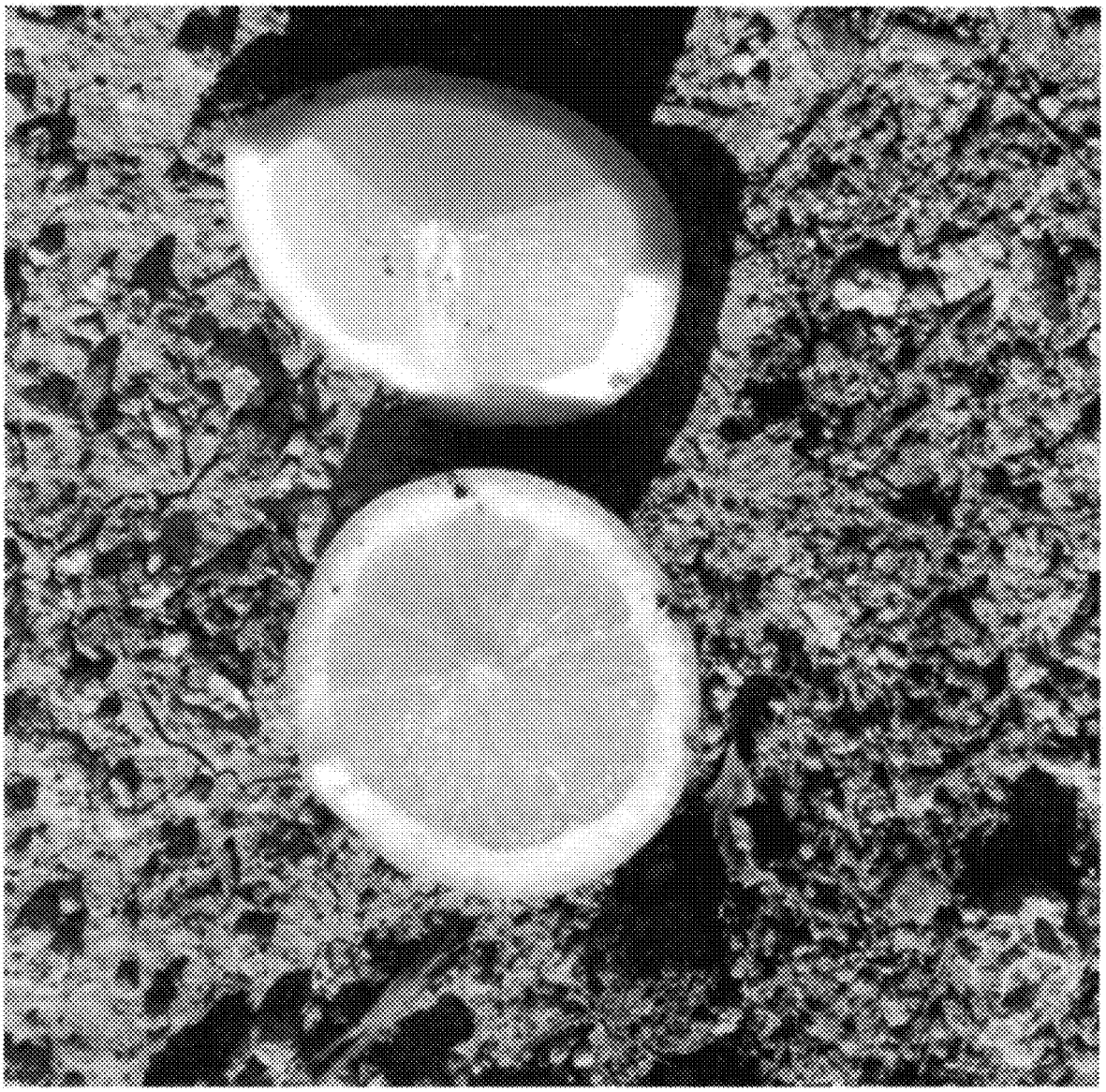
FIG. 7 is a photograph showing a cross-section attractive typical specimens of the mature fruit of 'BENEDICTO' at the time of harvest (typically during October).

The described plants of the new cultivar had been asexually reproduced by grafting on *Citrus macrophylla* rootstock (non-patented) outdoors in full sunlight in the Alicante region of Spain. The new cultivar was grafted with this new variety in April 2015 and observations obtained during the growing season of 2021 are presented.

Classification: *Citrus lemon* (L.) Burm. f.

Breeding scheme: Spontaneous mutation of the 'Fino 95' lemon tree.

Method of propagation of the variety: Vegetatively propagated by grafting on rootstock.

Characteristics of the variety:

*Young leaf.*—Presence of anthocyanin coloration: Present.

*Young leaf.*—Intensity of anthocyanin coloration: Medium.

*Fruit length.*—87.25±6.99 mm.

*Fruit diameter.*—67.68±3.92 mm.

*Fruit.*—Presence of neck: Absent.

*Fruit.*—Presence of nipple: Present.

*Fruit surface.*—Predominant color: Medium yellow, Group 150C, obtained from UPOV revision of document tgp/14: section 2: botanical terms: subsection 3: color: annex: Color names for The R.H.S. Color Chart. Fifty-Fourth Session Geneva, Oct. 29 and 30, 2018.

*Fruit.*—Main color of flesh: Light yellow, Group 8C, obtained from UPOV revision of document tgp/14: section 2: botanical terms: subsection 3: color: annex: Color names for The R.H.S. Color Chart. Fifty-Fourth Session Geneva, Oct. 29 and 30, 2018.

*Parthenocarpy.*—Present.

*Seedless.*—

*Juiciness.*—High.

*The growth habit of the claimed plant.*—Upright.

*The position of the broadest part of the fruit.*—At middle.

*The presence of depression at the stalk end.*—Absent.

*The thickness of the fruit rind.*—Medium.

*The oiliness of the fruit rind.*—Medium.

*The glossiness of the fruit surface.*—Medium.

*The polyembryony of the seed.*—Seedless.

*The flowering habit of the plant.*—Flowering more than once.

*The time of maturity of fruit for consumption.*—Early/medium.

The table below shows the physicochemical characteristics of the variety 'BENEDICTO' compared to the reference varieties 'Fino 95' and 'Fino 49' under homogeneous growing conditions on 25 Nov. 2021.

| Nov. 25, 2021 | 'Benedicto' | 'Fino 95' | 'Fino 49' |
|---|---|---|---|
| Weight (g) | 184.26 ± 31.46 | 195.93 ± 28.71 | 154.34 ± 20.61 |
| Diameter (mm) | 67.68 ± 3.92 | 69.09 ± 4.42 | 64.50 ± 2.58 |
| Esp corteza (mm) | 5.75 ± 1.00 | 6.09 ± 0.86 | 5.00 ± 0.85 |
| Crust thickness (g) | 99.46 ± 18.71 | 111.62 ± 19.44 | 82.50 ± 19.10 |
| Juiciness (mL/100 g) | 41.58 ± 5.29 | 37.74 ± 5.84 | 39.64 ± 8.76 |
| SS (°Brix) | 8.45 ± 0.21 | 8.55 ± 0.19 | 8.48 ± 0.41 |
| AT (g ac cit/100 mL) | 62.10 ± 4.32 | 56.57 ± 2.00 | 57.35 ± 2.94 |
| Maturity Index | 1.37 ± 0.12 | 1.51 ± 0.08 | 1.48 ± 0.10 |

What is claimed is:

1. A new and distinct variety of lemon plant named 'BENEDICTO' substantially as illustrated and described herein.

* * * * *